United States Patent [19]

Narita et al.

[11] 4,406,754

[45] Sep. 27, 1983

[54] METHOD AND PROBE FOR THE RAPID DETERMINATION OF SULFUR LEVEL

[75] Inventors: Kiichi Narita; Toshio Onoye; Akira Egami, all of Kobe, Japan

[73] Assignee: Kabushiki Kaisha Kobe Seiko Sho, Kobe, Japan

[21] Appl. No.: 246,944

[22] Filed: Mar. 24, 1981

[30] Foreign Application Priority Data

Mar. 28, 1980 [JP] Japan .................................. 55-41090
Dec. 10, 1980 [JP] Japan ................................. 55-174249

[51] Int. Cl.³ ........................................... G01N 27/46
[52] U.S. Cl. ..................................... 204/1 T; 204/424
[58] Field of Search .............. 204/1 S, 195 S; 429/33, 429/191

[56] References Cited

U.S. PATENT DOCUMENTS

| | | | |
|---|---|---|---|
| 3,578,578 | 5/1971 | von Krusenstierna | 204/195 S |
| 3,758,397 | 9/1973 | Rittiger et al. | 204/195 S |
| 3,827,913 | 8/1974 | Butherus et al. | 429/191 |
| 3,980,543 | 9/1976 | Eckfeldt | 204/195 S |
| 4,060,667 | 11/1977 | Askew et al. | 429/191 |
| 4,115,633 | 9/1978 | Kasper et al. | 429/191 |
| 4,136,233 | 1/1979 | Eisenberg | 429/191 |
| 4,237,201 | 12/1980 | Rolixel et al. | 429/191 |
| 4,246,081 | 1/1981 | Winnick | 204/195 S |
| 4,282,078 | 8/1981 | Chamberland et al. | 204/195 S |

OTHER PUBLICATIONS

*Science*, vol. 204, No. 4400, Jun. 19, 1979, pp. 1371-1379.
*J. Electrochem. Soc.*, vol. 118, No. 6, Jun. 1971, pp. 841-846.

*Primary Examiner*—T. Tung
*Attorney, Agent, or Firm*—Oblon, Fisher, Spivak, McClelland & Maier

[57] ABSTRACT

A method for rapidly determining a sulfur level in materials, particularly molten metals or gases, the method comprising contacting a reference electrode made of a specific type of a metal and metal sulfide mixture with a sulfur-containing molten metal or gas serving also as a counter electrode through a sulfide solid electrolyte thereby measuring an electromotive force established between the electrodes. The working temperature of the molten metal or gas is also measured. These parameters measured are used to calculate a sulfur content based on a certain equation. The probe for carrying out the above method is also disclosed, which comprises a reference electrode made of a material having a certain sulfur potential, a mass of a solid electrolyte comprised of CaS and TiS₂, the reference electrode being contacted with a molten metal or gas through the solid mass to form a cell, a means for measuring an electromotive force generated across the cell, and a means for measuring a working temperature of the molten metal or gas.

23 Claims, 17 Drawing Figures

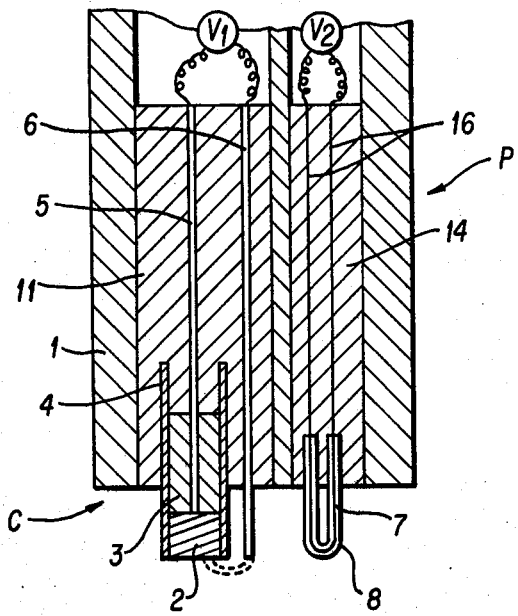
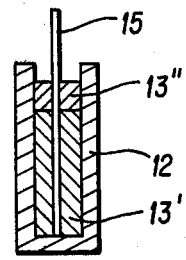
FIG. 1
FIG. 9
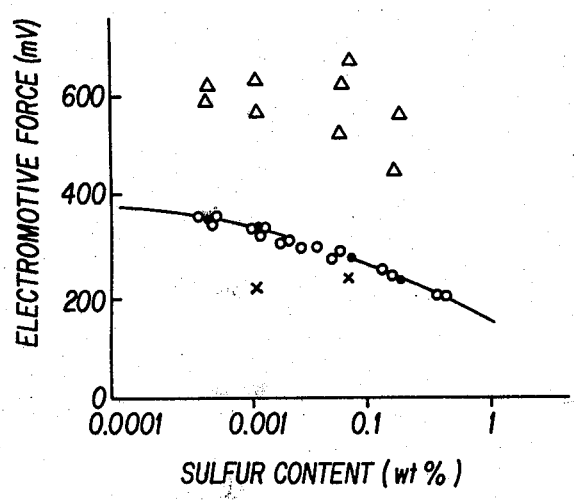
FIG. 8

METHOD AND PROBE FOR THE RAPID DETERMINATION OF SULFUR LEVEL

BACKGROUND OF THE INVENTION

1. Field of the Invention

This invention relates to the determination of a sulfur level in materials and more particularly, to a method and probe for the rapid determination of a sulfur level or content in molten metals or a partial pressure of sulfur in gases.

2. Description of the Prior Art

It is well known that sulfur in metals such as of pig iron and steels (including alloys) generally give rise to problems such as of deteriorating properties, particularly mechanical strengths, of iron and steel materials except for specific types of materials such as sulfur-containing free-cutting steel. Accordingly, it is necessary to invariably monitor a sulfur level at the time of manufacturing iron and steel so as to keep the sulfur level within a range suitable for individual materials. In order to properly control the sulfur level in these iron and steel materials, it is very important how to determine and analyze the sulfur.

Sulfur has been heretofore analyzed by several methods such as a gravimetric method, a neutralization titration method, an iodometric method and a pararose-aniline absorptiometric method (these methods being prescribed in JIS 1215). All of these methods are disadvantageous in that the analysis time is as long as 10 to several tens minutes. In this connection, there is also known a method in which the sulfur level in metal is measured by an infrared absorption technique (which method being not prescribed in the JIS standards). This method has a merit that the analysis time is an short as 1 to 2 minutes but has a drawback that a great deal of skill is required for sampling and thus a total length of time including the time for sampling and conveying samples is about 5 to 10 minutes and is thus relatively large.

For instance, in the refining of iron and steel, when a long time is required for the analysis of sulfur by the above-mentioned analyzing methods, during the course of desulfurization treatments of molten iron such as in iron ladle, torpedo car, mixer as well as at tapping of blast furnace, or during the desulfurization of molten steel such as in steel ladle as well as at blowing and tapping in converter, there arise problems that proper control of an iron or steel is delayed to give a product of a formulation below standards and that a waiting time for re-blowing and re-treatment becomes long, leading to a much lowering of productivity.

In order to overcome the above problems, the present inventors have made a study on and developed a method of rapidly determining a sulfur level in iron or steel, which has been proposed in Japanese Patent Application No. 31748/1979 and now laid open as a Laid-open No. 124061/1980. Further, we have presented the results of a study, entitled "Electrical Conductivities of CaS-base Solid Sulfides" at the meeting of Japan Institute of Metals on April, 1979. In "Metallurgische Elektrochemie" (1975), at pages 426-427 W. A. Fischer and D. Janke proposed their determination of sulfur in molten copper. Moreover, Ono et al of Kyoto University have published their research work, entitled "Measurement of Partial Pressure of Sulfur by an Electromotive Force method using Sulfide-base Solid Electrolytes" at the meeting of Mining and Metallurgical Institute of Japan, 1980 (publication of preliminary collection of lectures: Apr. 1, 1980).

However, any of these methods are not necessarily satisfactory in practical applications. Then, the present inventors have continued the studies along the line of the idea proposed in Japanese Patent Application No. 31748/1979 and found an improved method and probe effective for the practical applications.

SUMMARY OF THE INVENTION

It is an object of the present invention to provide a method for rapidly determining a sulfur content or level in materials which overcomes the prior art disadvantages described above.

It is another object of the invention to provide a method for the rapid determination of a sulfur level which is highly reliable and accurately and is feasible within a very short period of time.

It is a further object of the invention to provide the method by which a sulfur level in materials, particularly in molten iron or steel, can be relatively easily determined in an atmosphere of air or oxidative gas without being adversely influenced by oxygen in such atmosphere.

It is a still further object of the invention to provide a probe for carrying out the above method which is simple in construction.

These objects can be achieved, in one aspect according to the invention, by a method for the rapid determination of a sulfur level in materials which comprises contacting a reference electrode made of a material having a certain sulfur potential with a sulfur-containing molten metal or gas, to be measured, serving as a counter electrode through a sulfide solid electrolyte substantially composed of a major proportion of CaS and a minor proportion of $TiS_2$ to form a cell thereby measuring an electromotive force established between the reference and counter electrodes, measuring a working temperature of the counter electrode, and calculating a sulfur content from the two parameters of the electromotive force and the working temperature. The calculation is made based on the following equation:

$$E = \frac{RT}{4F} \ln \frac{p_{s2}(I)}{p_{s2}(II)}$$

in which $p_{s2}(I)$ and $p_{s2}(II)$ are, respectively, partial pressures of sulfur of the reference electrode and the counter electrode of a liquid or gas phase which is a material to be measured, E is an electromotive force measured, R is a gas constant, T is the absolute temperature, and F is the Faraday's constant.

According to another aspect of the invention, there is provided a probe for the rapid determination of a sulfur level which comprises a reference electrode made of a material having a certain sulfur potential, a mass of a solid electrolyte substantially composed of a major proportion of CaS and a minor proportion of $TiS_2$ and electrically contacted with the reference electrode, the reference electrode being contacted with a sulfur-containing molten metal or gas, to be measured, serving as a counter electrode through the solid electrolyte mass to form a cell, a means for measuring an electromotive force generated across the cell, and a means for measuring a working temperature of the molten metal or gas to be measured.

The above and other objects, features and advantages of the present invention will become apparent from the following description and the appended claims, taken in conjunction with the accompanying drawings.

BRIEF DESCRIPTION OF THE DRAWINGS

In the accompanying drawings:

FIG. 1 is a schematic view, in cross section, of a probe for the rapid determination of sulfur in materials according to the invention;

FIG. 8 is a graph showing a relation between electromotive force and sulfur level obtained according to a preferred embodiment of the invention in comparison with those obtained by different manners of the measurement; and FIG. 9 is a schematic view showing a modified cell of the probe according to the invention.

DETAILED DESCRIPTION OF THE INVENTION AND PREFERRED EMBODIMENTS

Figure 2A:
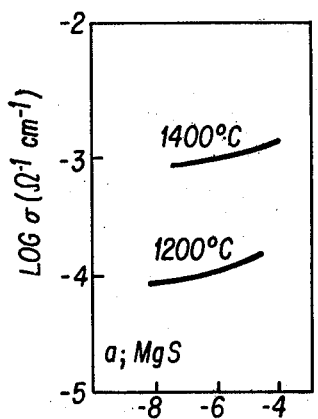
FIGS. 2a through 2i are graphs showing electrical conductivity of different types of sulfide in relation to partial pressure of sulfur.

Referring now to the accompanying drawings and particularly to FIG. 1, there is shown a probe, generally indicated at p, according to the invention. The probe p includes an apparatus body 1 having a mass of a sulfide solid electrolyte and a reference electrode 3 which is covered with or accommodated in a refractory tube or hollow cylinder 4 so that at least the bottom of the mass 2 is exposed. The reference electrode 3 is made of a material having a certain sulfur potential and is brought into contact with the solid electrolyte mass 2 which is to be contacted at the exposed bottom thereof with a molten metal or other materials (not shown) containing sulfur, thereby forming a cell C for measuring an electromotive force generated between the reference electrode 3 and a counter electrode. As a matter of course, the cell C includes a lead 5 electrically connected to the solid electrolyte mass 2 and the reference electrode 3 at one end thereof as shown and a lead 6 which contacts with the counter electrode at its free end. In the case of measurement of partial pressure of sulfur in gas, the counter electrode 6 must contact with the solid electrolyte mass 2. At the other end, the leads 5, 6 are connected to a means for measuring the electromotive force such as a volt meter $v_1$. The cell C is held to the apparatus body 1 through a solid mass 11 made of an electrically insulating, refractory material such as alumina cement. The probe further includes a temperature detecting unit T for measuring the temperature of the molten metal or gas. The unit T has a Pt thermocouple 7 accommodated in a silica tube 8, which is secured to the apparatus body 1 through a solid mass 14 of a refractory material. The solid masses 11 and 14 are fixed to the apparatus body. The cell C and the temperature detecting unit T extend from the apparatus body at the lower ends thereof so as to be partly immersed in the molten metal. The temperature detecting unit is connected to a means such as a volt meter $v_2$ through a pair of electrodes 16.

By immersing the probe of the just-described arrangement in molten metal or by exposing the probe in high temperature gas, the electromotive force and temperature can be measured by means of the cell and the detecting unit, respectively. From these values a sulfur content in the molten metal or partial pressure of sulfur in the gas can be calculated using an equation which will be explained hereinbelow.

As is apparently seen from the above, the present invention is based on a principle that there is formed a cell which comprises a reference electrode made of a material having a certain sulfur potential, a molten metal or gas to be measured being used as a counter electrode, and a mass of a solid electrolyte of a specific type connected between the electrodes, and a sulfur content in the molten metal or gas is determined from an electromotive force of the cell and a temperature of the molten metal or gas. The cell has such an arrangement as mentioned below.

Lead wire/Reference electrode, $p_{s2}(I)$/Solid electrolyte/Material to be measured, $p_{s2}(II)$/Lead wire in which $p_{ps2}(I)$ and $p_{s2}(II)$ represent partial pressures of sulfur of the reference electrode and the molten metal or gas electrode, respectively. In the case, when the ionic transport number of the solid electrolyte is 1, the electromotive force E of this concentration cell is given by the following equation (i.e. the Nernst's equation):

$$E = \frac{RT}{4F} \ln \frac{p_{s2}(I)}{p_{s2}(II)} \tag{1}$$

in which R is a gas constant and F is the Faraday's constant.

Then it is the most important in the practice of the invention what material is used as the solid electrolyte mass interposed between the electrodes so as to constitute the cell. That is, it is not too much to say that the measuring system of the invention is vitally influenced by the solid electrolyte.

This electrolyte is essentially required at a temperature where the probe is working (1) to show ion conductivity, (2) to be chemically stable to molten metal or gas, and (3) to show high electrical conductivity. These requirements should be satisfied at the same time. The requirement (1) is necessary for a reason which follows: In principle, the electromotive force generates by a difference in sulfur potential (activity or concentration) between the electrodes and thus charges have to be carried by ions through the solid electrolyte. The requirement (2) means that when the probe of the invention is immersed in molten metal or gas, the solid electrolyte is not changed in quality by reaction with molten metal or components (e.g. dissolved oxygen) contained therein and gas or is not dissolved in molten metal or the like. The requirement (3) must be satisfied since too low electrical conductivity results in a great internal resistance of the cell, so that when the electromotive force is measured, a response becomes so dull as to involve a difficulty in rapid measurement.

Various types of sulfide have been checked to know their physical and chemical properties such as electrical conductivity, heat conductivity, free energy of formation, and crystal structure and, as a result, it has been found that sulfides of alkali metal and alkaline earth metal can satisfy the requirement (1) or show the ion conductivity. All of the alkali sulfides having melting points of below 1000° C. and are in liquid state at temperatures at which molten copper or iron can exist. In addition, they are high in vapor pressure and reactive and thus are not usable as a solid electrolyte. On the other hand, the alkaline earth sulfides having melting points of above 2000° C. and have a possibility of being applied as solid electrolyte at temperatures below these melting points.

Figure 2B:
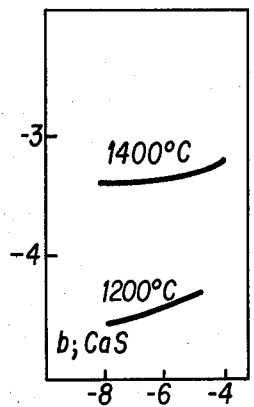
Figure 2C:
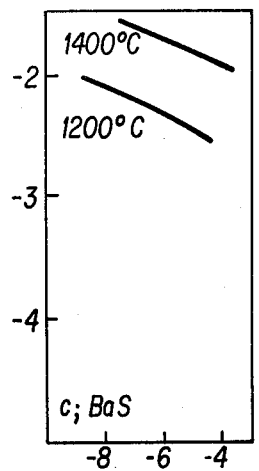
Figure 3:
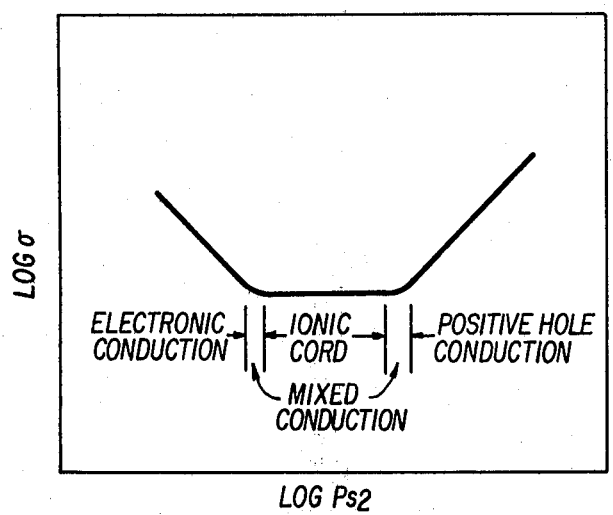
FIG. 3 is a graph schematically showing different modes of electrical conductivity in relation to partial pressure of sulfur.

Then, alkaline earth sulfides have been subjected to the measurement of electrical conductivity. In FIGS. 2a to 2c, there are shown influences of a partial pressure of sulfur on the electrical conductivities of magnesium sulfide (MgS), calcium sulfide (CaS) and barium sulfide (BaS) at 1200° C. and 1400° C., respectively. These values were accurately determined by pressing each of powders of various sulfides into a cylindrical form, sintering it at 1600° C. for 12 hours to give a sample, and then subjecting the sample to an ac bridge-complex impedance plot method in atmospheres of mixed gases of hydrogen and hydrogen sulfide having different partial pressures of sulfur. From these values there can be evaluated not only electrical conductivity but also ionic conductivity from the dependence of the partial pressure of sulfur. That is, when the logarithm of the electrical conductivity is plotted against the logarithm of the partial pressure of sulfur as shown in FIG. 3, an electronic conduction appears in case where the electrical conductivity is negative in gradiant with respect to the partial pressure of sulfur, a positive hole conduction appears in the case of positive gradient and an ionic conduction appears if the electrical conductivity is independent of the partial pressure of sulfur. It will be noted that in regions where the electrical conductivity is changed from the electronic conduction to ionic conduction or from the ionic conduction to positive hole conduction, there exist mixed conduction regions where two types of the conductions are present in the respective cases. Accordingly, the solid electrolyte should have an electrical conductivity in a region of ionic conduction which is not dependent on an ambient partial pressure of sulfur. As for the requirement (1), whether it is satisfied or not can be evaluated by measuring an electrical conductivity under varying conditions of the partial pressure of sulfur.

As is clearly seen from FIGS. 2a and 2b, MgS and CaS show the positive hole conduction at a high level of sulfur partial pressure and the ionic conduction at low sulfur partial pressure. On the other hand, as shown in FIG. 2c, BaS shows an higher electrical conductivity than MgS and CaS due to the electronic conduction.

From a standpoint of stability to molten metal, MgS is susceptible to oxidation at high temperatures and undergoes a reaction with oxygen contained in molten metal when measured not only in an atmosphere of air but also in an inert atmosphere and is thus converted into MgO. BaS was readily reacted with molten metal (iron) and a satisfactory measurement of the electromotive force could not be made. Accordingly, both MgS and BaS do not satisfy the requirement (2). On the other hand, CaS was recognized to have such a high melting point as of above 2500° C. and to be chemically stable to molten metals (copper, iron, etc.) of high temperature.

The above investigation and experimental results are summarized in Table 1 below, from which it is found that CaS is most suitable as a solid electrolyte except a disadvantage which will be described later.

TABLE 1

| | Sulfide | Melting Point (°C.) | Conduction mechanism | Reactivity with Molten Metal (iron, copper) | Electrical Conductivity ($\times 10^{-6} \Omega^{-1} cm^{-1}$) | |
|---|---|---|---|---|---|---|
| | | | | | 1200° C. | 1400° C. |
| alkali metal | Na$_2$S | 920 | Na$^+$ conduction | reactive | liquid | liquid |
| | K$_2$S | 840 | K$^+$ conduction | reactive | liquid | liquid |
| alkaline earth metal | MgS | 2000 | Mg$^{2+}$ conduction | oxidized | 0.9 | 8 |
| | CaS | 2525 | Ca$^{2+}$ conduction | stable | 0.3 | 6 |
| | BaS | 2200 | electronic conduction | reactive | 71 | 320 |

The disadvantage of CaS is that its electrical conductivity is low. In order to increase the electrical conductivity of Ca$^{2+}$ in CaS, we have made an experiment in which a sulfide having a cation of a higher valence than that of Ca is added in small amounts.

Figure 2D:
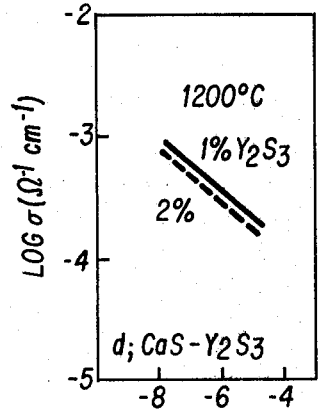
Figure 2E:
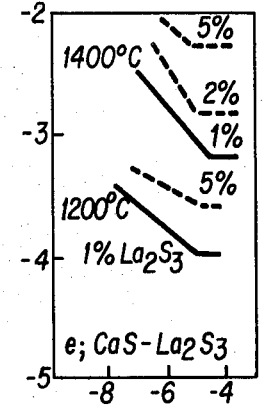
Figure 2F:
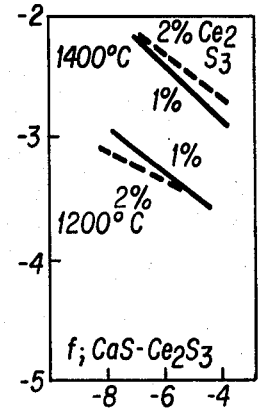
Figure 2G:
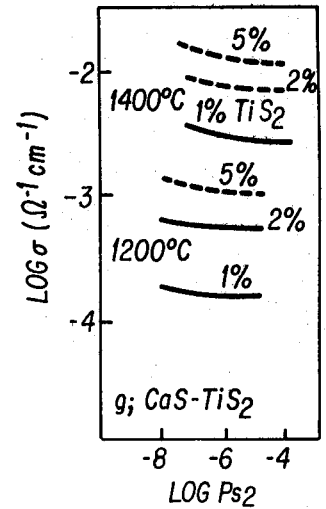
Figure 2H:
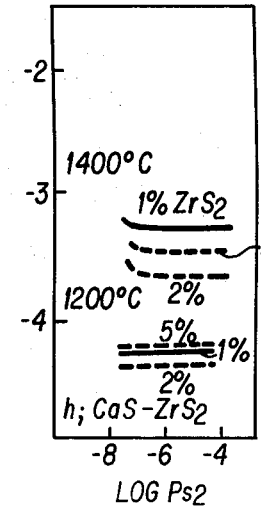
Figure 2I:
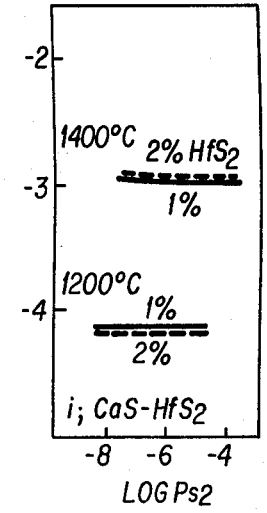

FIGS. 2d–2f show the dependence of the partial pressure of sulfur on the electrical conductivity at 1200° C. and 1400° C. when 1–5 wt% of sulfides of trivalent rare earth metals, i.e. yttrium (Y), lanthanum (La) and cerium (Ce), are added and FIGS. 2g–2i show such dependence when sulfides of titanium group elements of tetravalence, i.e. titanium (Ti), zirconium (Zr) and hafnium (Hf), are added in amounts of 1–5 wt%, respectively.

As is seen from these figures, the electrical conductivities of CaS to which the rare earth sulfide become greater by 3–10 times than that of CaS alone but electronic conduction appears particularly at a lower side of the partial pressure of sulfur, thus impeding the inherent ionic conductivity.

CaS to which the titanium group sulfides are added generally shows ionic conductivity held at a level though a slight degree of electronic conduction appears at a low level of sulfur. The electrical conductivities of CaS to which ZrS$_2$ and HfS$_2$ are added are low but that of CaS added with TiS$_2$ is 8–30 times as high as those of CaS.

From a viewpoint of the requirements (1) and (2) among the three requirements for the solid electrolyte, the titanium group sulfides, TiS$_2$, ZrS$_2$ and HfS$_2$, are preferable to the the rare earth sulfides as those to be added to CaS. Further, in order to satisfy the requirement (3), TiS$_2$ shows the most excellent effect of addition among the titanium group sulfides.

The following experiment was conducted to investigate in more detail the ionic conductivity of the sulfides whose main component was CaS.

These sulfide electrolytes were used to make cells. The cells were each immersed in a carbon-saturated molten iron containing sulfur at 1200°-1500° C., followed by measuring its electromotive force. The electromotive force is expressed by the following equation in which partial electronic conduction is taken into account in the equation (1):

$$E = \frac{RT}{F} \ln \frac{p_e^{\frac{1}{4}} + p_{s2}(I)^{\frac{1}{4}}}{p_e^{\frac{1}{4}} + p_{s2}(II)^{\frac{1}{4}}}, \quad p_{s2}(II) = \left(\frac{[\%\,S]}{K'_s}\right)^2 \quad (2)$$

in which:
E: electromotive force (V)
T: absolute temperature (K.)
R: gas constant, 1.9865 calK$^{-1}$ mol$^{-1}$
F: Faraday's constant, 23066 cal V$^{-1}$ mol$^{-1}$
$p_e$: parameter of partial electronic conduction of solid electrolyte, atm
$p_{s2}(I)$: partial pressure of sulfur (at the side of reference electrode), atm
$p_{s2}(II)$: partial pressure of sulfur (at the side of molten iron electrode), atm
[%S]: sulfur content in molten metal
$K'_s$: apparent equilibrium constant of reaction; $\frac{1}{2}S_2=S$ The parameter ($p_e$) of the partial electronic conduction of solid electrolyte is intended to mean an index showing a degree of the ionic conductivity in an ionic conductor containing a small degree of electronic conduction. A material in which the above parameter is zero is a complete ionic conductor. That is, a small value of the parameter shows a greater proportion of ionic conduction. When the content of sulfur is determined by a chemical analysis, $p_e$ can be determined from the equation (2) using the electromotive force and temperature of the molten metal.

Figure 4:
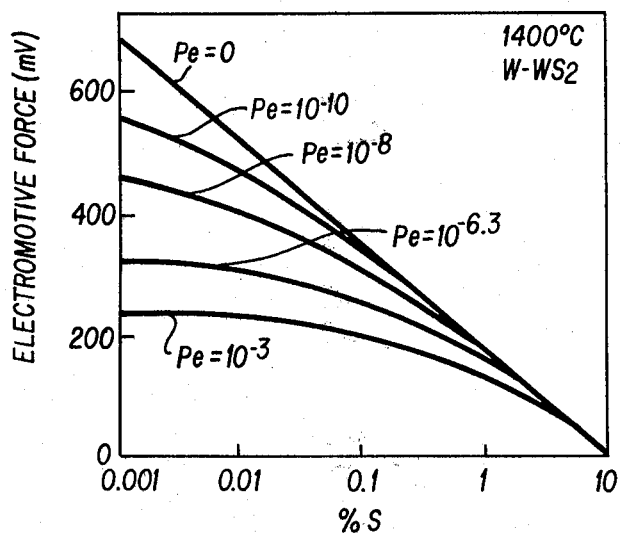
FIG. 4 is a graph showing a relation between electromotive force and sulfur level for different partial electronic conductivity parameters $p_e$.

In FIG. 4, there is shown a relation between the electromotive force and the content of sulfur for different values of $p_e$ in accordance with the equation (2). This is a case where the reference electrode is a mixture of W+WS$_2$. When $p_e$ is zero, the electromotive force becomes linear in relation to the logarithm of the content of sulfur. As $p_e$ increases, a variation of the electromotive force in relation to the content of sulfur becomes small especially in a region of low contents of sulfur. In order to measure at high accuracy sulfur of a concentration as low as 0.002-0.02% such as in molten iron or steel, it is desirable that $p_e < 10^{-6.3} \simeq 5 \times 10^{-7}$.

As for the electrical conductivity ($\sigma$), where the electrolyte is formed into a mass having a size of, for example, 5$\phi \times$5 mm, the solid electrolyte mass has a resistance of below 2 K$\Omega$. Upon measurement of the resistance of the mass using a volt meter of an input resistance of 1 M$\Omega$ which is ordinarily used for the measurement of electromotive force, an error of the measurement is within a range of below 0.2%. In order to facilitate the response, the electrical conductivity should be $\sigma > 1.3 \times 10^{-3} \Omega^{-1} cm^{-1}$.

Figure 5:
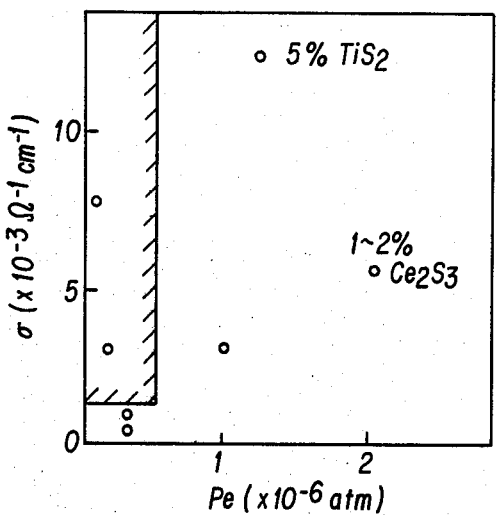
FIG. 5 is a graph showing a relation between partial electronic conductivity parameter $p_e$ and electrical conductivity for different types of sulfide at a temperature of 1,400° C.

FIG. 5 shows a relation between $p_e$ and $\sigma$ at 1400° C. for different sulfide compositions whose major component is CaS. An optimum region as solid electrolyte is indicated by the shadowed portion where $\sigma > 1.3 \times 10^{-3} \Omega^{-1} cm^{-1}$ and $p_e < 5 \times 10^{-7}$ atm, from which it is found that compositions of CaS containing 1 and 2 wt% of TiS$_2$ are within the optimum range and CaS containing small amounts of TiS$_2$ are again recognized as optimum.

Figure 6:
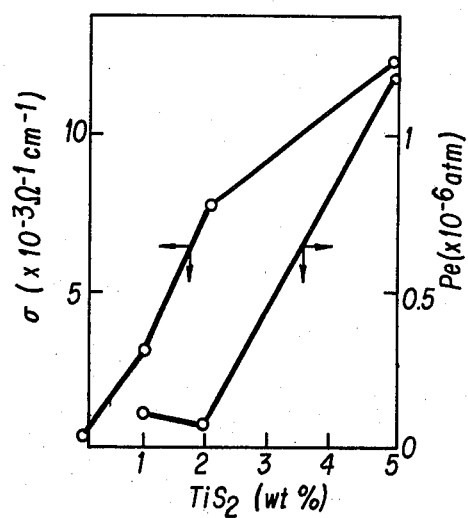
FIG. 6 is a graph showing the parameter of partial electronic conductivity $p_e$ and the electrical conductivity of $CaS$-$TiS_2$ sulfide in relation to variation in amount of $TiS_2$.

FIG. 6 shows an influence of TiS$_2$ on $p_e$ and $\sigma$ of CaS-TiS$_2$ sulfides. The amount of TiS$_2$ which satisfies the optimum region of the solid electrolyte is in the range of 0.4-3.5% by weight.

Figure 7:
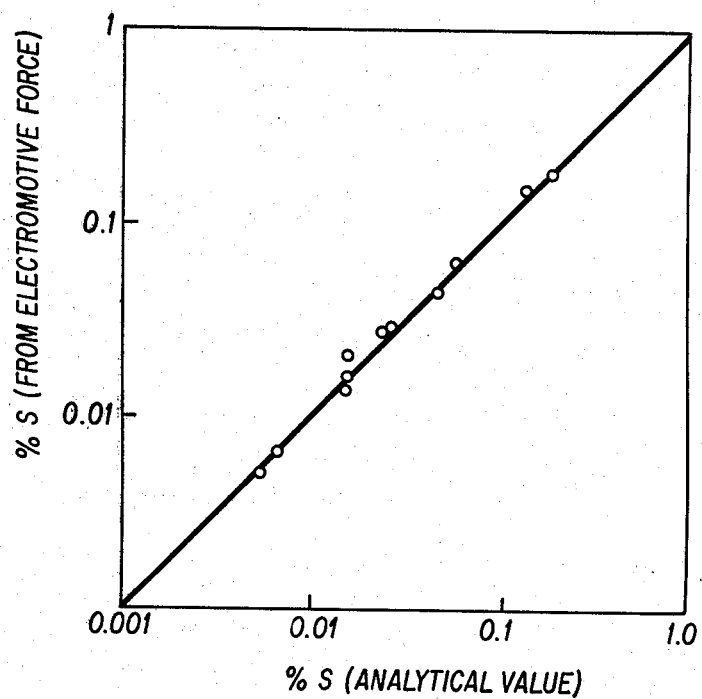
FIG. 7 is a graph showing an interrelation between a sulfur level in a molden iron saturated with carbon at a temperature of 1,400° C. which is measured according to the present invention and a sulfur level measured by chemical analysis.

Then, there is shown in FIG. 7 a relation between a content of sulfur obtained from the afore-indicated equation using the electromotive force and temperature which are obtained by immersing the cell in a carbon saturated molten iron (1400° C.) containing different amounts of sulfur and a value obtained by the chemical analysis of sulfur which is highly reliable. The reference electrode is made of a mixture of W+WS$_2$ and the sulfide solid electrolyte mass is made of CaS−2% TiS$_2$.

As is apparent from FIG. 7, a close interrelation is observed and thus the accuracy of the method of the invention is recognized to be very high.

Then, the reference electrode is described which is made of a material having a certain sulfur potential.

The reference electrode is made of a material such as a powdery mixture of a metal and a sulfide thereof e.g. Cr+CrS, Mn+MnS, Mo+Mo$_2$S$_3$ or W+WS$_2$, a metal containing sulfur, or an alloy such as Fe-0.01% S.

The leads for the reference electrode and molten metal or gas serving as a counter electrode are preferably made of Mo, W or Fe. In consideration of the influence of the thermoelectromotive force, it is preferable that a metal of the same type as used in both electrodes is used.

In the practice of the invention, the reference electrode and the sulfide solid electrolyte mass are protected on their side surfaces with a refractory tube such as an alumina tube, silica tube or magnesia tube. Similarly, the thermocouple for measuring the temperature of molten metal or gas is accommodated in a heat-resistant tube such as a silica tube. The thermocouple is generally of the Pt type, such as, for example, Pt-Pt13Rh.

According to the method and probe for the rapid determination of a sulfur level in particularly molten metal of the invention, the sulfur content in the metal can be measured rapidly, i.e. within a period of about 4-10 seconds, at high accuracy. In addition, the method and probe are very simple in principle and construction.

A further embodiment of the invention will be described.

When a sulfur level or content in a molten metal, for example molten iron is measured, it is found that in an Ar atmosphere the electromotive force produced fairly corresponds to sulfur contact as seen in FIG. 8 and indicated by mark "o". In this connection, however, when the sulfur content in molten iron is measured in air or in an oxidative atmosphere, it has been sometimes experienced that the electromotive force tends to be measured at a higher level and does not precisely correspond to sulfur content, thus making it difficult or impossible to make a quantitative determination of sulfur. As a result of the investigation made by the present inventors, it has been found that such tendency is caused by oxygen in the atmosphere which serves to oxidize the reference electrode.

The influence of oxygen on the electromotive force by the oxidation of the reference electrode is described.

In practice, the reference electrode used to measure the sulfur content in molten metal is, as described hereinbefore, made of a two-phase equilibrium mixture of a metal and its sulfide. The oxide or sulfate produced by oxidation of the reference electrode gives an influence on the partial pressure of sulfur even though such oxidation proceeds only in a slight degree, leading to a great variation of the electromotive force. When the reference electrode is oxidized the equilibrium partial pressure of sulfur of the reference electrode $p_{s2}(I)$ varies simultaneously with the generation of a partial pressure of oxygen between the reference and counter electrodes. Accordingly, the generated electromotive force results from a mixture of the partial pressures of oxygen and sulfur and thus does not show a value corresponding to the sulfur content in the molten metal.

It is necessary to suppress the reference electrode from being oxidized to an extent as low as possible. The countermeasure is feasible by the following methods.

(1) The reference electrode is tightly sealed and shut off from the oxidative atmosphere.

(2) The atmosphere of the reference electrode is properly controlled.

(3) A getter for oxygen is provided around the reference electrode.

However, in the case of (1), it is difficult to hermetically seal the reference electrode completely. The tight sealing may damage the mass of the solid electrolyte by a pressure exerted thereon during the increase of temperature, coupled with another problem that even though the electrode is completely sealed, there can not be eliminated oxygen which is originally incorporated in interstices of powders of a metal and metal sulfide constituting the reference electrode. In the case of (2), it is considered to feed an inert gas such as argon to the reference electrode or enclose the reference electrode in a case where the inert gas is filled. The former requires additional pump and pipings for the feed and is thus inconvenient and complicated. The filling of the gas involves a difficulty in completely enclosing the electrode at such a high temperature as of molten metal. Even though the filling is realized, an influence of pressure at the time of temperature rise must be taken into account, thus presenting a problem in practical applications.

A simple method for overcoming the problems of the methods (1) and (2) is the method (3). For instance, when there are used readily oxidizable metals such as Mg, Ca, Ti, Zr and the like which are known as typical oxygen getters, it is sure that oxygen can be removed but there is produced a disadvantage that metal oxides formed during the removal give an adverse influence on the partial pressure of sulfur and an accurate electromotive force can not be obtained. Then, the present inventors have made a further studied on the method (3) in which a number of experiments and tests have been made to select materials which are optimumly applicable as an oxygen getter.

That is, in order to prevent the reference electrode constituted of metal M and metal sulfide $MS_x$ from being oxidized, another type of metal sulfide $M'S_y$ which is more susceptible to oxidation than M and $MS_x$ is admixed with or present in the metal sulfide mixture. In the case, it is important that the sulfide $M'S_y$ or $M'O_y$ formed by oxidation of the sulfide gives little or no influence on the electromotive force of the reference electrode.

In order to allow the sulfide $M'S_y$ of another type to be more susceptible to oxidation than the metal sulfide $MS_x$, an absolute value of a change in free energy $\Delta G$ of the reaction; $M'S_y+(Y/2)O_2=M'O_y+(Y/2)S_2$ has to be greater than that of the reactions; $MS_y+(X/2)O_2=MO_x+(X/2)S_2$. Further, in order that another sulfide $M'S_y$ or produced oxide $M'O_y$ does not give any influence on the partial pressure of sulfur $p_{s2}(I)$, the equilibrium sulfur partial pressure of $M'$ and $M'S_y$ must be lower than $p_{s2}(I)$ and the equilibrium oxygen partial pressure of $M'$ and $M'O_y$ must be extremely low.

Moreover, the metal sulfide $MS_x$ and another sulfide $M'S_y$ more susceptible to oxidation do not solve with each other nor form an intermediate compound $MM'_wS_z$ in a solid state. In addition, their mutual solubility must be as small as possible.

As described hereinbefore, the metal and metal sulfide constituting the reference electrode are for example, combinations of W and $WS_2$, Mo and $Mo_2S_3$, Cr and CrS, Mn and MnS and the like. Suitable examples of another sulfides susceptible to oxidation include alkali earth sulfides such as MgS, CaS, etc. rare earth sulfides such as $Y_2S_3$, $La_2S_3$, $Ce_2S_3$, etc. and titanium group sulfides such as $TiS_2$, $ZrS_2$, $HfS_2$, etc. Preferably, the another sulfides are contained in an amount of not more than 20 wt% of the materials constituting the reference electrode. When the amount exceeds 20 wt%, there is a tendency that a reaction takes place between the metal sulfides of the different types.

In order to permit the sulfide of another type to coexist in the reference electrode, it may be directly mixed with the metal and metal sulfide to be constituents of the reference electrode or may be placed on the upper side of the electrode which is usually exposed to the atmosphere containing oxygen. Alternatively, the both manners of the application may be used.

In order to clarify the excellent effect of the above embodiment, a sulfur level has been measured using the reference electrode where a metal sulfide of another type is incorporated, in comparison with known or the other methods described hereinbefore. In FIG. 8, there is shown a relation between an electromotive force of each sample determined by the sulfur level measuring device or probe of FIG. 1 and a sulfur level obtained from the electromotive force and temperature. In the figure, the mark "●" indicates a case where the reference electrode is made of a mixture of $W+WS_2$ admixed with 5 wt% of MgS, the mark "Δ" indicates a case where the reference electrode is made of W and $WS_2$ along without making any measure to counter oxidation, and the mark "x" indicates a case where the reference electrode is made of $W+WS_2$ and Ar gas is fed to the electrode at a rate of 300 cc/min to preclude the oxidation. It will be noted that in order to ensure the accuracy of these results of the measurement, a reference electrode made of $W+WS_2$ is used to measure a sulfur level in an Ar atmosphere with the results shown by the mark "o".

As is seen from FIG. 8, in the case indicated by the mark "x", the reference electrode is found to be prevented from being oxidized to a certain extent but owing to a lowering of the temperature of the reference electrode involved by the feed of Ar, the electromotive force becomes lower as compared with that determined in the Ar atmosphere. With the case of "Δ", the electromotive force becomes abnormally high by the influence of oxygen in the atmosphere this method can not be used at all in view of its poor accuracy of measurement. The results of the embodiment according to the invention indicated by "●" coincide with those obtained by the measurement in the Ar atmosphere and thus the measurement can be conducted in a very high efficiency.

A further embodiment of the probe according to the invention is shown in FIG. 9, in which the cell C is made of solid electrolyte 12 instead of a refractory material other than the solid electrolyte in FIG. 1. The cell C is in the form of U in section or in the form of a crucible, in which a reference electrode 13' is accommodated. A lead 15 is inserted into the crucible 12 so that it electrically contacts with the electrode 13' and the crucible 12 as shown. By the arrangement, the reference electrode can be protected from being directly contacted with a material to be measured as will be experienced when a breakage takes place between the solid electrolyte 2 and the refractory tube 4 of FIG. 1 for some reasons or other. Further, the reference electrode 13' of FIG. 9 may be superposed or covered thereon with a layer 13" of a metal sulfide which is more susceptible to oxidation than the metal and the metal sulfide which are components of the reference electrode 13'. This precludes oxygen from entering the reference electrode. Of course, the reference electrode may be made of a mixture of a metal and sulfide thereof further admixed with a metal sulfide more susceptible to oxidation than the first-mentioned sulfide and serving as an oxygen getter.

As will be seen from the foregoing, the method and probe for the rapid determination of a sulfur level in material according to the invention has a number of advantages that the sulfur level can be determined within a very short time and accurately without suffering any influence of oxygen in air or an oxidative atmosphere and that the probe is simple in construction.

What is claimed is:

1. A method for the rapid determination of a sulfur level in material which comprises contacting a sulfur-containing material, to be measured, serving as a counter electrode, with a sulfide solid electrolyte comprising CaS and 0.4–3.5% by wt. of $TiS_2$, said sulfide solid electrolyte being in contact with a reference electrode made of a material having a certain sulfur potential, to form a cell, measuring the electromotive force generated between the reference and counter electrodes, measuring the working temperature of the counter electrode, and calculating a sulfur level from the two parameters of the electromotive force and working temperature.

2. A method according to claim 1, wherein said reference electrode is protected from oxygen.

3. A method according to claim 1, wherein said reference electrode comprises a mixture of a metal and a sulfide thereof having a certain sulfur potential.

4. A method according to claim 3, wherein said mixture is a combination of W and $WS_2$, Mo and $Mo_2S_3$, Cr and CrS or Mn and MnS.

5. A method according to claim 1, or 4, wherein the reference electrode is made of a mixture of a metal and a sulfide thereof, and a sulfide which is different from and more susceptible to oxidation than the metal and the first-mentioned sulfide.

6. A method according to claim 5, wherein the sulfide which is more susceptible to oxidation is a member selected from the group consisting of alkaline earth sulfides of MgS and CaS, rare earth sulfides of $La_2S_3$ and $Ce_2S_3$ and titanium group sulfides of $TiS_2$, $ZrS_2$ and $HfS_2$.

7. A probe for the rapid determination of a sulfur level in material which comprises a reference electrode made of a material having a certain sulfur potential, a mass of a solid electrolyte comprising CaS and 0.4–3.5% by wt. of $TiS_2$ and electrically contacted with said reference electrode to one surface thereof, said solid electrolyte being contactable with a sulfur-containing molten metal or gas, to be measured, serving as a counter electrode through said solid electrolyte mass to form a cell, a means for measuring an electromotive force generated across said cell, a means for measuring the temperature of the molten metal or gas to be measured, and a pair of leads connecting said reference electrode and said counter electrode, respectively, to said means for measuring an electromotive force.

8. A probe according to claim 7, wherein said reference electrode and said solid electrolyte mass are covered with a tube of a refractory material except that at least the bottom of said solid electrolyte mass is exposed to allow contact thereof with the sulfur-containing molten metal or gas.

9. A probe according to claim 7, wherein said reference electrode comprises a mixture of a metal and a sulfide thereof.

10. A probe according to claim 9, wherein the mixture is a combination of W and $WS_2$, Mo and $Mo_2S_3$, Cr and CrS or Mn and MnS.

11. A probe according to any of claims 7 and 9 wherein said reference electrode is made of a mixture of a metal and sulfide thereof, and a metal sulfide other than the first-mentioned metal sulfide, the second-mentioned metal sulfide being more susceptible to oxidation than the metal and the first-mentioned metal sulfide.

12. A probe according to claim 11, wherein said second-mentioned metal sulfide is a member selected from the group consisting of alkaline earth sulfides of MgS and CaS, rare earth sulfides of $La_2S_3$ and $Ce_2S_3$ and titanium group sulfides of $TiS_2$, $ZrS_2$ and $HfS_2$.

13. A probe according to claim 12, wherein said second-mentioned metal sulfide is contained in an amount of not more than 20 wt% of a composition for constituting the reference electrode.

14. A probe according to claim 9, wherein said reference electrode is covered thereon with a layer of a metal sulfide which is more susceptible to oxidation than the metal and a sulfide thereof constituting said reference electrode, said metal sulfide being a member selected from the group consisting of alkaline earth sulfides of MgS and CaS, rare earth sulfides of $La_2S_3$ and $Ce_2S_3$ and titanium group sulfides of $TiS_2$, $ZrS_2$ and $HfS_2$, the metal and sulfide thereof being a member selected from the group consisting of combinations of W and $WS_2$, Mo and $Mo_2S_3$, Cr and CrS and Mn and MnS.

15. A probe according to claim 14, wherein said metal and sulfide thereof further comprise not more than 20 wt.% of MgS, CaS, $La_2S_3$, $Ce_2S_3$, $TiS_2$, $ZrS_2$ or $HfS_2$.

16. A probe according to claims 14 or 15, wherein the combination is W and $WS_2$ and said metal sulfide is MgS.

17. A probe according to claim 7, wherein said reference electrode is Fe-0.01% S alloy.

18. A probe according to claim 7, wherein said solid electrolyte mass is in the form of U in section, in which said reference electrode is accommodated.

19. A probe according to claim 7, wherein said reference electrode, said solid electrolyte mass, and said pair of leads are held fixed to an apparatus body through an electrically insulating, refractory material.

20. A probe according to claim 7, wherein the temperature-measuring means includes a thermocouple, a casing enclosing the thermocouple therein, a pair of leads each connected to the thermocouple at one end thereof, and a means connected to the thermocouple through said pair of leads to read the temperature of the molten metal or gas.

21. A probe according to claim 7, wherein said pair of leads are each made of a metal of the same type as used in said reference electrode.

22. A probe according to claim 7, wherein the electromotive force-measuring means includes a pair of leads one of which is electrically connected to both said reference electrode and said solid electrolyte mass, the other lead being connected with the said electrolyte mass to allow the measurement of sulfur partial pressure in a gas.

23. A probe according to claim 6, wherein said pair of leads are each made of a metal of the same type as used in said reference electrode.

* * * * *

UNITED STATES PATENT AND TRADEMARK OFFICE
CERTIFICATE OF CORRECTION

PATENT NO. : 4,406,754

DATED : September 27, 1983

INVENTOR(S) : NARITA ET AL.

It is certified that error appears in the above-identified patent and that said Letters Patent is hereby corrected as shown below:

In column 14, line 6, delete "6" and insert therefor --22--.

Signed and Sealed this

Tenth Day of April 1984

[SEAL]

Attest:

GERALD J. MOSSINGHOFF

Attesting Officer

Commissioner of Patents and Trademarks